United States Patent [19]

Tokuda et al.

[11] Patent Number: 5,376,552
[45] Date of Patent: Dec. 27, 1994

[54] USE OF PHENOL DERIVATIVE IN COLORIMETRIC ANALYSIS OF METAL IONS

[75] Inventors: Kuniaki Tokuda; Taeko Soma; Naoki Teno, all of Kawagoe, Japan

[73] Assignee: Wako Pure Chemical Industries, Ltd., Osaka, Japan

[21] Appl. No.: 970,643

[22] Filed: Nov. 2, 1992

Related U.S. Application Data

[63] Continuation of Ser. No. 623,632, Dec. 6, 1990, abandoned.

[30] Foreign Application Priority Data

Dec. 7, 1989 [JP] Japan .................................. 1-318285

[51] Int. Cl.$^5$ ............................................. G01N 21/78
[52] U.S. Cl. ........................................ 436/73; 436/74; 436/79; 436/166
[58] Field of Search ...................... 436/73–74, 436/76–77, 79–84, 164, 166, 815

[56] References Cited

U.S. PATENT DOCUMENTS

| | | | |
|---|---|---|---|
| 3,754,865 | 8/1973 | Gindler | 436/74 X |
| 4,503,156 | 3/1985 | Yamazato et al. | 436/79 |
| 4,588,695 | 5/1986 | Takano et al. | 436/74 X |
| 4,942,107 | 7/1990 | Saeki et al. | 430/138 |
| 4,962,009 | 10/1990 | Washizu et al. | 430/138 |
| 5,221,626 | 6/1993 | Yamazato et al. | 436/74 |

FOREIGN PATENT DOCUMENTS

| | | |
|---|---|---|
| 0068875 | 1/1983 | European Pat. Off. . |
| 2217007 | 10/1989 | United Kingdom . |
| 0525666 | 8/1976 | U.S.S.R. . |
| 0734194 | 5/1980 | U.S.S.R. . |

OTHER PUBLICATIONS

Reilly, C. N.; "Chelometric Titrations", Analytical Chemistry, 37(11), (1965) pp. 1298–1300.
Voronina, N. M. et al, "3-Methoxy-4-hydroxy-5-dicarboxy-methyl-aminomethyl benzophenone prepared from methoxy hydroxy-benzoquinone for use as complexing agent showing reduced affinity to calcium," World Patent Index Accession No. 81-18831D/11, Abstract.
Chemical Abstracts, vol. 86, No. 21, May 23 1977, p. 445, abstract No. 155374z.
Chemical Abstracts, vol. 87, No. 17, Oct. 24, 1977, p. 658, abstract No. 134322m.
Chemical Abstracts, vol. 103, No. 19, Nov. 11, 1985, p. 675, abstract No. 160165f.
Chemical Abstracts, vol. 94, No. 8, Feb. 23, 1981, p. 440, abstract No. 53825v.
Journal of General Chemistry of The USSR, vol. 51, No. 3, Mar. 1981, pp. 528–531.

*Primary Examiner*—Jeffrey R. Snay
*Attorney, Agent, or Firm*—Armstrong, Westerman, Hattori, McLeland & Naughton

[57] ABSTRACT

A phenol derivative obtained by reacting a carboxylic acid anhydride with a phenol compound, followed by condensation with iminodiacetic acid and formaldehyde, or a salt thereof is effective as an agent for adjusting color forming sensitivity in a colorimetric analysis of metal ions in a fluid such as a living body fluid.

4 Claims, 7 Drawing Sheets

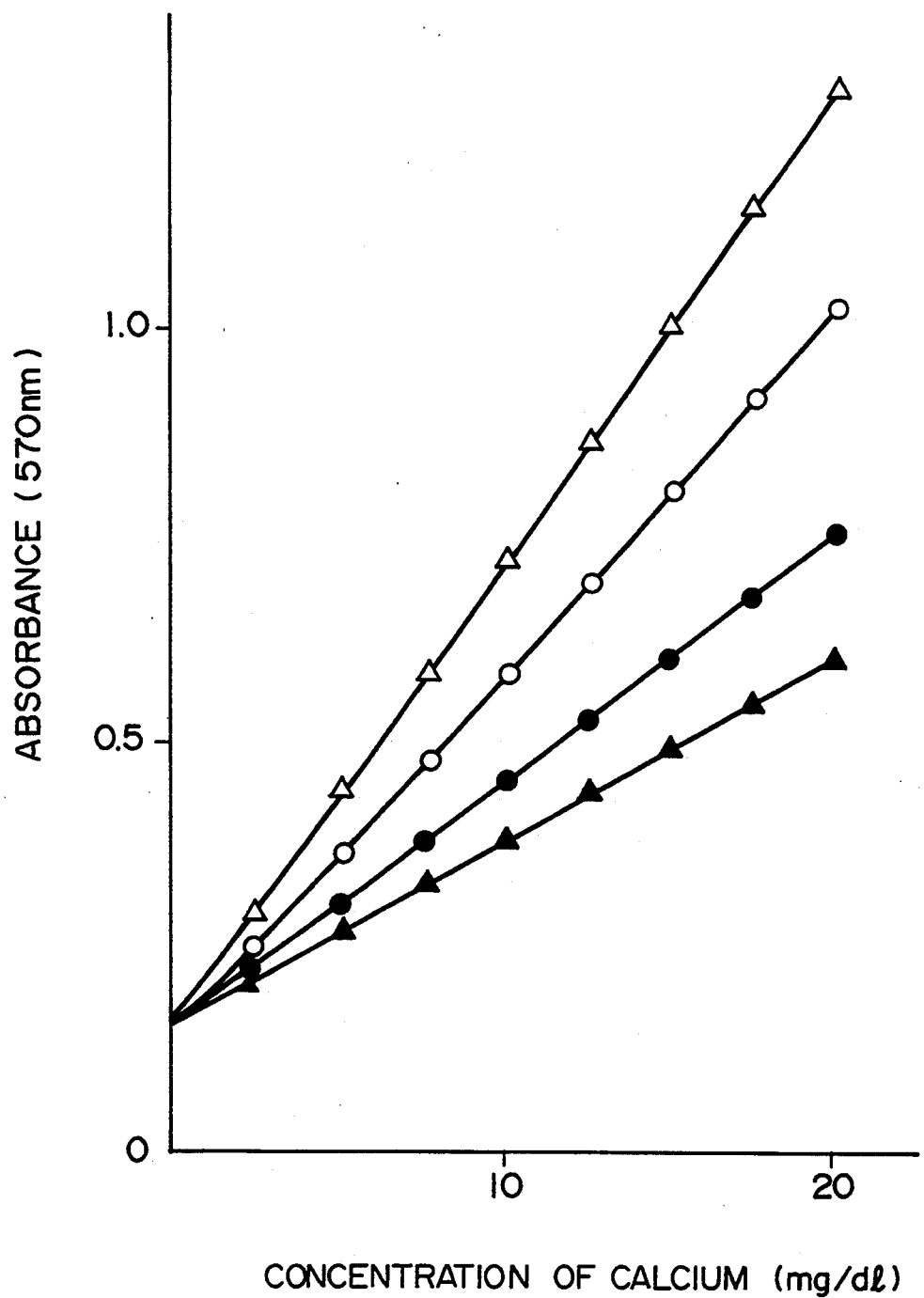
F I G. 1

F I G. 2
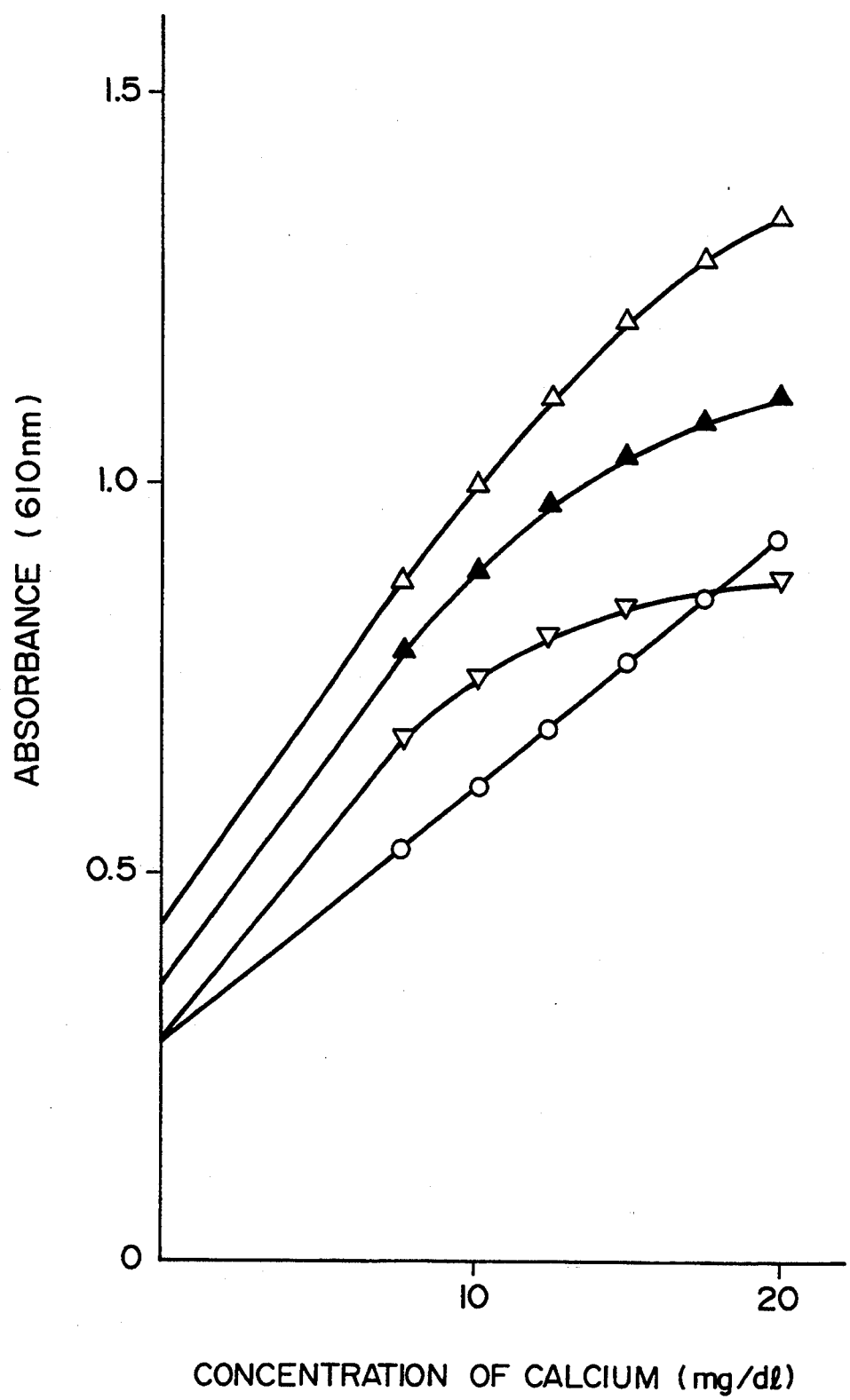

F I G. 6
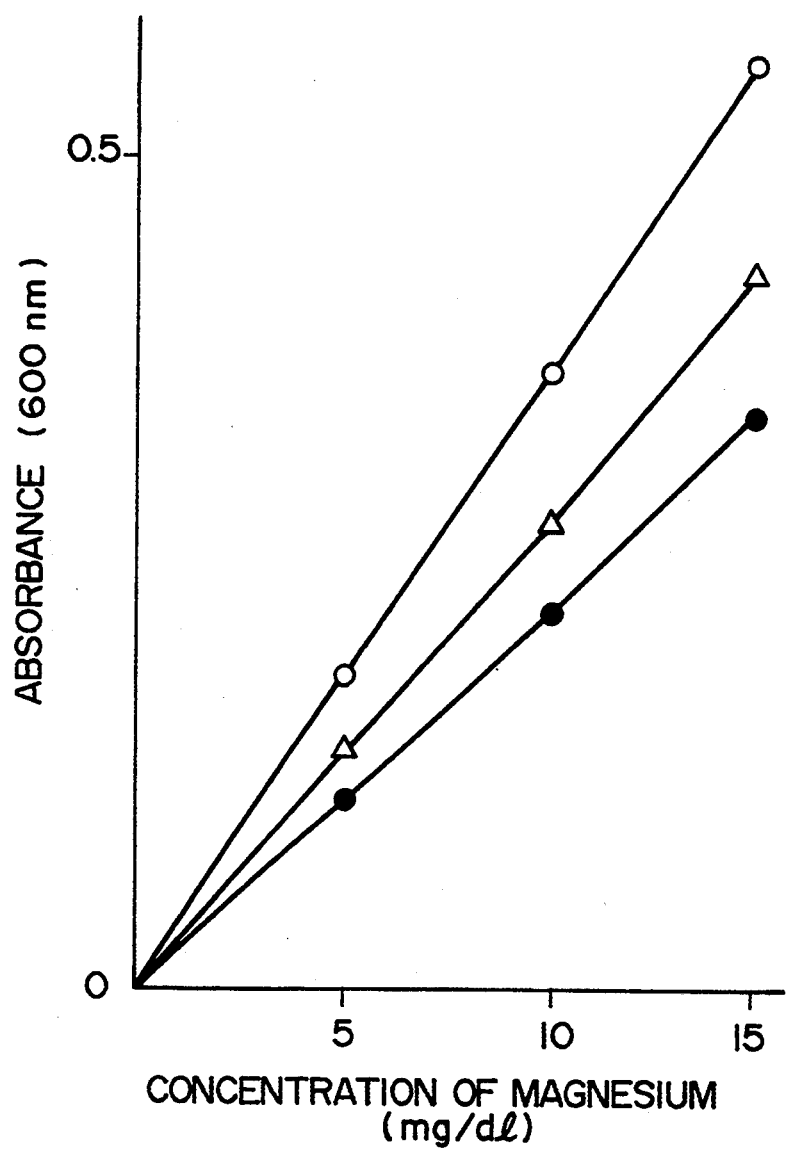

USE OF PHENOL DERIVATIVE IN COLORIMETRIC ANALYSIS OF METAL IONS

This application is a continuation of application Ser. No. 623,632 filed Dec. 6, 1990, now abandoned.

BACKGROUND OF THE INVENTION

This invention relates to a phenol derivative or a salt thereof, which can be utilized as an agent for adjusting sensitivity at the time of measurement in a method for a colorimetric analysis of metal ions by use of a chelating reagent; and a process for using said phenol derivative or salt thereof as an agent for adjusting sensitivity for a colorimetric analysis of metal ions.

Methods for a colorimetric analysis of metal ions by use of a chelating reagent capable of forming a chelate with metal ions to develop a color have a relatively high precision and require only easy operations. Therefore, they are widely utilized in the fields of water quality analysis, clinical chemical analysis, etc.

On the other hand, the chelating reagent used for such a purpose is required to have a high specificity, a large chelate formation constant, etc. Accordingly, usable chelating reagents are limited as a matter of course, depending on the kind of metal ion. For example, for analysis for calcium, there are used chelating reagent such as phthalein complexone (OCPC), Methylxylenol Blue (MXB), Methylthymol Blue (MTB), etc. For analysis for magnesium, there are used chelating reagents such as Xylylazo Violet (XB-I), etc.

However, the molecular extinction coefficient ($\epsilon$) of a chelate formed by the reaction of any of the above-exemplified chelating reagents with metal ions (hereinafter abbreviated as "color forming sensitivity") has a relatively high value. Therefore, in the case of carrying out measurement for a sample containing a high concentration of metal ions to be measured, for example, the case of measuring calcium or magnesium in serum, the problem ① or ② described below is caused, resulting in low reliability on the analysis result, unless color forming sensitivity at the time of measurement is adjusted by some method.

① When the sampling amount of the sample for analysis is determined so that the variation of the sampling amount may have substantially no influence on a measured value, the calibration range for analysis is narrowed unless the total amount of reagent solution used for the measurement is increased to some extent.

② When the sampling amount of the sample is reduced for reducing the total amount of reagent solution used for the measurement, the within-run precision is lowered, and the influence of soiling of instruments used is enhanced as much.

Particularly when analysis for calcium or magnesium in serum is carried out by means of an automatic analyzer having restrictions such as the lower limit of the sampling amount of a sample and the upper limit of the sampling amount of reagent for analysis, it is very difficult to maintain a satisfactory within-run precision and a suitable calibration range, unless the color forming sensitivity at the time of measurement is adjusted by a suitable method.

As a method for adjusting the color forming sensitivity in such a measurement as described above, there are known, for example, a method of placing, in a reaction system, citric acid, tartaric acid or the like, which reacts with metal ions to form a colorless chelate, and a method using a carbonate buffer solution as a buffer solution for measurement. However, the former method is disadvantageous in that the reliability of measured values is lowered because the constant of chelate formation by citric acid or the like and the constant of chelate formation by a chelating reagent vary greatly with temperature. The latter method has, for example, the following disadvantages. The concentration of the buffer should be high for preventing the pH from being lowered by the absorption of carbon dioxide in the air, but when it is too high, the color forming sensitivity is greatly lowered, so that the measurement is hindered. Moreover, the buffer solution has a buffer capacity only in a narrow pH range, and therefore the kind of usable chelating reagent is limited.

SUMMARY OF THE INVENTION

The present invention was made in consideration of such conditions and is intended to provide a phenol derivative or a salt thereof, which is similar to a chelating reagent used, in the degree of change of the constant of chelate formation with temperature, and forms a colorless chelate with metal ions; and a process for a colorimetric analysis of metal ions by use of said phenol derivative or salt thereof as an agent for adjusting color forming sensitivity.

The present invention provides a phenol derivative of the formula [I], or a salt thereof:

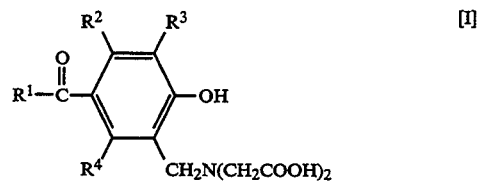

wherein $R^1$ is a hydroxyl group, a halogen atom, an alkyl group which may have one or more substituents, an aryl group which may have one or more substituents, or a heterocyclic group which may have one or more substituents; $R^2$ to $R^4$ are independently a hydrogen atom, a lower alkyl group, a lower alkoxy group or a halogen atom.

The present invention also provides a process for using the phenol derivative of the formula [I] or a salt thereof as a color forming sensitivity adjusting agent in a colorimetric analysis of metal ions.

Moreover, the present invention provides a process for producing the phenol derivatives of the formula [I].

BRIEF DESCRIPTION OF THE DRAWINGS

FIG. 1 shows calibration curves obtained in Example 2 and Comparative Examples 1 and 2.

FIG. 2 shows calibration curves obtained in Example 3 and Comparative Example 3.

FIG. 6 and FIG. 7 show calibration curves obtained in Example 6.

DESCRIPTION OF THE PREFERRED EMBODIMENTS

Figure 3:
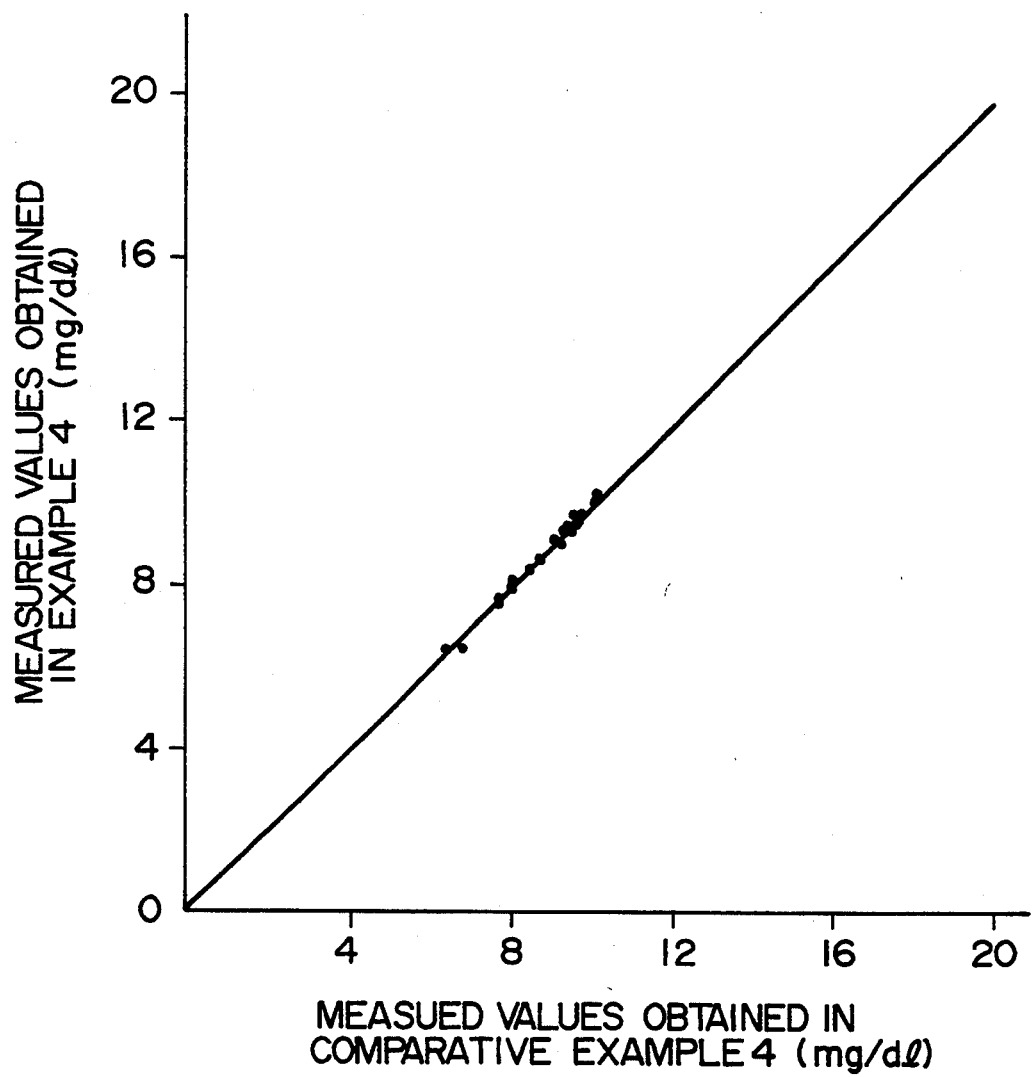
FIG. 3 shows correlation diagram prepared on the basis of measured values obtained by Example 4 and Comparative Example 4.

In order to attain a calibration range suitable for a sample to be analyzed, in a method for a colorimetric analysis of metal ions by use of a chelating reagent, the present inventors investigated in search of a method which permits proper adjustment of the color forming sensitivity of various chelating reagents. Consequently, the present inventors found that when the phenol derivative of the above formula [I] or a salt thereof is properly present in a reagent solution during measurement, the color forming sensitivity of various chelating reagents can be properly adjusted with substantially no influence of measurement conditions such as temperature change, whereby the present invention was accomplished.

The phenol derivative of this invention is represented by the following formula:

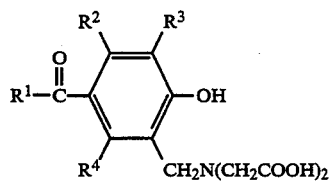

[I]

wherein $R^1$ is a hydroxyl group, a halogen atom, an alkyl group which may have one or more substituents, an aryl group which may have one or more substituents, or a heterocyclic group which may have one or more substituents; $R^2$ to $R^4$ are independently a hydrogen atom, a lower alkyl group, a lower alkoxy group or a halogen atom.

In the formula [I], for $R^1$, the halogen atom includes, for example, iodine, chlorine, bromine and fluorine. The alkyl group of the alkyl group which may have one or more substituents includes, for example methyl group, ethyl group, propyl group and butyl group (which may be either linear or branched), and the substituents include, for example, halogen atoms (e.g. iodine, chlorine, bromine and fluorine), hydroxyl group, carboxyl group and sulfonic group. The aryl group of the aryl group which may have one or more substituents include, for example, phenyl group and naphthyl group, and the substituents include, for example, hydroxyl group, carboxyl group, sulfonic group, alkyl groups (e.g. methyl group, ethyl group, propyl group and butyl group) which may be either linear or branched, and halogen atoms (e.g. iodine, chlorine, bromine and fluorine). The heterocyclic group of the heterocyclic group which may have one or more substituents includes, for example, pyridyl group, piperazino group, piperidino group, imidazolyl group and morpholino group, and the substituents include, for example, hydroxyl group, carboxyl group, sulfonic group, alkyl groups (e.g. methyl group, ethyl group, propyl group and butyl group) which may be either linear or branched, and halogen atoms (e.g. iodine, chlorine, bromine and fluorine).

As the atom or the group which $R^2$ to $R^4$ independently represent, there can be exemplified hydrogen atom, lower alkyl groups (e.g. methyl group, ethyl group, propyl group and butyl group) which may be either linear or branched, lower alkoxy groups (e.g. methoxy group, ethoxy group, propoxy group and butoxy group) which may be either linear or branched, and halogen atoms (e.g. iodine, chlorine, bromine and fluorine).

The phenol derivative of the formula [I] may be in the form of a salt with ammonia, an alkali metal (e.g. sodium or potassium), an organic amine (e.g. tris(hydroxymethyl)aminomethane, triethanolamine or monoethanolamine), or the like.

Concrete examples of the formula (I) are as follows:

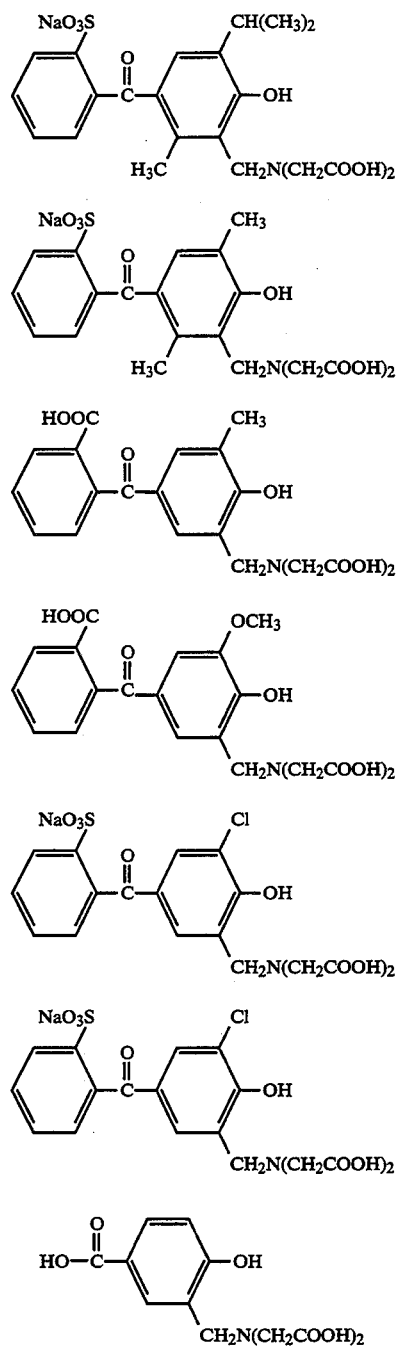

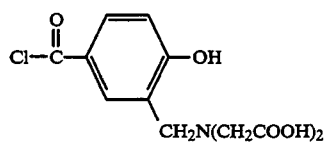

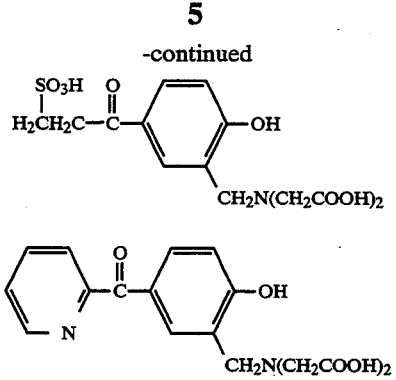

The phenol derivative of the formula [I] can easily be synthesized in the following manner.

One mole of a carboxylic acid anhydride such as sulfobenzoic anhydride, phthalic anhydride, acetic anhydride or the like is subjected to condensation reaction with 0.5 to 1.5 moles of a phenol compound of the formula:

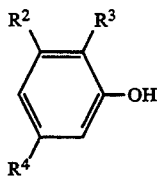

wherein $R^2$ to $R^4$ are as defined above, at room temperature to 130° C. in a solvent such as nitrobenzene, a halogenated hydrocarbon (e.g. 1,2-dichloroethane or chloroform) or the like, in the presence of a Lewis acid catalyst such as zinc chloride, aluminum chloride, fluoromethanesulfonic acid or the like. Then, the reaction product is condensed with iminodiacetic acid and formaldehyde under acidic conditions. Thus, the phenol derivative of the present invention can easily be synthesized.

At the phenol compound of the formula:

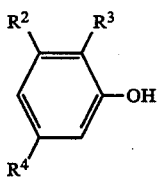

wherein $R^2$ to $R^4$ are as defined above, a commercial one may be used. When not commercially available, the phenol compound may be properly synthesized by a conventional method.

The phenol derivatives of the formula [I] or a salt thereof can be used as an agent for adjusting color forming sensitivity in a colorimetric analysis of metal ions.

When a metal ion which can form a color by reacting with a chelating agent is added to a solution containing both the chelating agent and the compound of the present invention, the metal ion reacts with the chelating agent and the compound of the present invention to form chelates individually. The forming ratio of the individual chelates is proportional to the ratio of the chelating agent and the compound of the present invention in the solution. Therefore, by changing the ratio of the compound of the present invention to the chelating agent in the solution, the forming ratio of the chelate obtained from the chelating agent and the metal ion (colored chelate) is changed, so that the color forming sensitivity of the chelating agent and the metal ion is regarded as changed (i.e. apparent color forming sensitivity changes).

The process of the present invention applies this phenomenon. The compound of the present invention is effective as an agent for adjusting color forming sensitivity of the chelating agent which forms a colored chelate by reacting with the metal ion.

It is sufficient that the process for a colorimetric analysis of metal ions of the present invention is practiced in accordance with a conventional analytical method except for using a reagent solution prepared by properly adding the phenol derivative of the formula [I] to a reagent solution for colorimetric analysis containing a chelating reagent conventionally used for measuring said metal ions.

That is, it is sufficient that the chelating reagent, a buffer, and optionally an antiseptic, a surfactant, etc., which are added to the reagent solution for analysis, are properly selected from those used in conventional methods, and are added in conventional concentration ranges. It is sufficient that the pH, temperature, reaction time and the like at the time of measurement are determined in accordance with a conventional method.

The chelating reagent includes, for example, phthalein complexone (OCPC), Methylxylenol Blue (MXB), Methylthymol Blue (MTB) and Xylylazo Violet (XB-I). The buffer includes, for example, monoethanolamine and boric acid.

As the phenol derivative of the formula [I] or a salt thereof, which is used in the analytical process of the present invention, there may be used either one of or a proper combination of two or more of phenol derivatives of the formula [I] or salt thereof. The concentration of the phenol derivative of the formula [I] or a salt thereof in the reagent solution for analysis is not critical and may be properly determined depending on the color forming sensitivity of the chelating reagent used and a desired calibration range. For example, when calcium in serum is measured by using phthalein complexone as the chelating reagent, said concentration is properly chosen in the range of usually 0.2 to 10 times, preferably 0.5 to 2 times, the molar concentration of phthalein complexone used. When calcium in serum is measured by using Methylxylenol Blue as the chelating reagent, said concentration is properly chosen in the range of usually 0.2 to 10 times, preferably 0.5 to 2 times, the molar concentration of Methylxylenol Blue used.

As metal ions measurable by the process of the present invention, any metal ions can be exemplified without a particular limitation so long as they can be measured by use of the above-exemplified chelating reagents. Preferable specific examples of such metal ions are ions of alkaline earth metals such as magnesium (Mg), calcium (Ca), strontium (Sr), barium (Ba), etc.; heavy metals such as indium (In), thorium (Th), bismuth (Bi), cadmium (Cd), mercury (Hg), cobalt (Co), ion (Fe), lead (Pb), zinc (Zn), etc.; and rare earth elements such as lanthanum (La), scandium (Sc), yttrium (Y), etc.

The process of the present invention can be widely utilized in the fields of water quality analysis, clinical chemical analysis, etc. As samples to which said process is applicable, there can be exemplified living body fluids (e.g. plasma, serum and urine), and industrial drain or waste water.

The present invention is more concretely explained below with reference to Examples, which are not by way of limitation but by way of illustration.

EXAMPLE 1

Synthesis of sodium 2-[3-[N,N-bis(carboxymethyl)aminomethyl]4-hydroxy-2,5-dimethylbenzoyl]benzenesulfonate (1) Synthesis of sodium 2-(4-hydroxy-2,5-dimethylbenzoyl)benzenesulfonate To a solution of 3 g of p-xylenol and 4.6 g of o-sulfobenzoic anhydride in 15 ml of dichloroethane was added dropwise 3.7 g of trifluoromethanesulfonic acid at 50° C., and the reaction was carried out with stirring at 50° C. for another 3 hours. After completion of the reaction, 70 ml of water was added to the reaction solution and the resulting solution was neutralized with NaOH, after which the aqueous layer was separated and then concentrated under reduced pressure. The resulting residue was purified by a silica gel chromatography (packing: Wakogel C-200 (trade name, mfd. by Wako Pure Chemical Industries, Ltd.), eluent: a mixed solvent of chloroform and methanol] to obtain 2 g of sodium 2-(4-hydroxy-2,5-dimethylbenzoyl)benzenesulfonate.

mp: 126°–128° C. UV: $\lambda_{max}$=215 nm ($\epsilon$=20×10³ in MeOH). IR $\upsilon cm^{-1}$(KBr): 3100(—OH), 1610(CO), 1580 (Phenyl), 1260–1140(SO₃H ). ¹HNMR $\delta$ppm (DMSO-$d_6$): 1.94(3H, s, O—C=C—CH₃), 2.42(3H, s, CH₃), 6.65(1H, s, Ar—H), 6.65–7.03, 7.36–7.41, 7.74–7.77(5H, m each, Ar—H).

(2) Synthesis of sodium 2-[3-(N,N-bis(carboxymethyl)aminomethyl]-4-hydroxy-2,5-dimethylbenzoyl]-benzenesulfonate 0.65 Gram of the sodium 2-(4-hydroxy-2,5-dimethylbenzoyl)benzenesulfonate obtained in (1) above, 0.28 g of iminodiacetic acid, 0.35 g of sodium acetate and 0.21 g of formaldehyde were reacted with stirring in 10 ml of acetic acid at 70° C. for 8 hours. After completion of the reaction, 50 ml of ethanol was added to the reaction solution to precipitate the desired compound. The crude crystals thus obtained were purified by a silica gel chromatography [packing: Wakogel C-200 (trade name mfd. by Wako Pure Chemical Industries, Ltd.), eluent: a mixed solvent of chloroform, methanol and water] to obtain 0.26 g of sodium 2-[3-[N,N-bis(carboxymethyl)aminomethyl]-4-hydroxy-2,5-dimethylbenzoyl]benzenesulfonate.

mp: 282° C. UV: $\lambda_{max}$=215 nm ($\epsilon$=26.5×10³ in Water). IR $\upsilon cm^{-1}$(KBr): 3200(—OH), 1630(CO), 1570 (Phenyl), 1260–1160(SO₃H). ¹HNMR $\delta$ppm (D₂O): 2.10(3H, s,

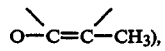

2.60(3H, s, CH₃), 3.28(4H, s, CH₂COOHx2), 4.66(2H, s, CH₂N<), 7.19(1H, s, Ar—H), 7.38, 7.66, 7.92(4H, m each, Ar—H).

EXAMPLE 2

Measurement of Calcium-1

Samples

Solutions containing predetermined concentrations of calcium (Ca²⁺) were used as samples.

Buffer Solution

There was used 5% monoethanolamine buffer (pH 11.0).

| [Color producing solution] | |
|---|---|
| Solution of phthalein complexone | 0.016% |
| sodium 2-[3-[N,N-bis(carboxymethyl)-aminomethyl]-4-hydroxy-2,5-dimethyl-benzoyl]benzenesulfonate | given conc. |
| oxine in 0.1 N hydrochloric acid | 0.4% |

Procedure

After 30 μl of each sample, 2.0 ml of the buffer solution and 0.5 ml of each color producing solution were thoroughly mixed and then allowed to stand at room temperature for 5 minutes, absorbance at 570 nm was measured.

Results

The measurement results thus obtained are shown in FIG. 1. FIG. 1 is a graph obtained by plotting absorbance (OD₅₇₀ ₙₘ) on the axis of ordinate corresponding to individual calcium concentrations on the axis of abscissa. In FIG. 1, -○- shows the results of measurement using the color producing solution containing 0.012% of sodium 2-[3-[N,N-bis(carboxymethyl)aminomethyl]-4-hydroxy-2,5-dimethylbenzoyl]benzenesulfonate, and the results of measurement using the color producing solution containing 0.024% of sodium 2-[3-[N,N--bis-(carboxymethyl)aminomethyl]-4-hydroxy-2,5-dimethyl-benzoyl]benzenesulfonate.

COMPARATIVE EXAMPLE 1

Measurement of Calcium

Samples

The same samples as in Example 2 were used.

Buffer Solution

The same buffer solution as in Example 2 was used.

| [Color producing solution] | |
|---|---|
| A solution of phthalein complexone | 0.016% |
| oxine in 0.1 N hydrochloric acid | 0.4% |

Procedure

Measurement was carried out in the same manner as in Example 2.

Results

The measurement results thus obtained are also shown in FIG. 1 (-Δ-).

COMPARATIVE EXAMPLE 2

Measurement of Calcium

Samples

The same samples as in Example 2 were used.

Buffer Solution

The same buffer solution as in Example 2 was used.

| [Color producing solution] | |
| --- | --- |
| A solution of phthalein complexone | 0.016% |
| oxine | 0.4% |
| citric acid | 0.21% |
| in 0.1 N hydrochloric acid | |

Procedure

Measurement was carried out in the same manner as in Example 2.

Results

The measurement results thus obtained are also shown in FIG. 1 (- -).

As is clear from FIG. 1, the color forming sensitivity can be adjusted by adding sodium 2-[3-[N,N-bis(carboxymethyl)aminomethyl]-4-hydroxy-2,5-dimethylbenzoyl]benzenesulfonate which is a phenol derivative of the present invention.

Table 1 shows the results of carrying out measurement at two measuring temperatures by using each of the color producing solutions described in Example 2, Comparative Example 1 and Comparative Example 2 and each of two samples, i.e., a calcium solution having a concentration of 100 mg/dl (a standard solution) and fresh human serum.

TABLE 1

| Reagent | Measuring temperature (°C.) | Blank test (570 nm) | Absorbance of standard solution (570 nm) | Measured value for human serum (mg/dl) 1 | 2 |
| --- | --- | --- | --- | --- | --- |
| E-2 | 20 | 0.158 | 0.295 | 7.4 | 9.6 |
|  | 37 | 0.140 | 0.242 | 7.4 | 9.6 |
| C-1 | 20 | 0.162 | 0.556 | 7.4 | 9.4 |
|  | 37 | 0.142 | 0.456 | 7.4 | 9.4 |
| C-2 | 20 | 0.153 | 0.225 | 7.6 | 9.7 |
|  | 37 | 0.130 | 0.123 | 7.8 | 9.8 |

In Table 1, the symbols E-2, C-1 and C-2 denote Example 2, Comparative Example 1 and Comparative Example 2, respectively.

As is clear from the results shown in Table 1, in Comparative Example 2 in which the sensitivity was lowered by adding citric acid, the color forming sensitivity varied greatly, depending on the measuring temperature, and variation of measured value was observed. In the case of the process of the present invention, the color forming sensitivity did not vary greatly, depending on the measuring temperature, and no variation of measured value was observed.

EXAMPLE 3

Measurement of Calcium-2

Samples

The same samples as in Example 2 were used.

Buffer Solution

There was used 5% monoethanolamine buffer (pH 12.0).

| [Color producing solution] | |
| --- | --- |
| Solution of Methylxylenol Blue | 0.016% |
| sodium 2-[3-[N,N-bis(carboxymethyl)-aminomethyl]-4-hydroxy-2,5-dimethylbenzoyl]benzenesulfonate | 0.011% |
| oxine | 0.4% |
| in 0.05 N hydrochloric acid | |

Procedure

After 50 μl of each sample, 2.0 ml of the buffer solution and 1.0 ml of the color producing solution were thoroughly mixed and then allowed to stand at room temperature for 5 minutes, absorbance at 610 nm was measured.

Results

The measurement results thus obtained are shown in FIG. 2 by -O-. FIG. 2 is a graph obtained by plotting absorbance ($OD_{610\ nm}$) on the axis of ordinate corresponding to individual calcium concentrations on the axis of abscissa.

COMPARATIVE EXAMPLE 3

Measurement of Calcium

Samples

The same samples as in Example 2 were used.

Buffer Solution

The same buffer solution as in Example 3 was used.

| [Color producing solutions] | |
| --- | --- |
| Solution of Methylxylenol Blue | given conc. |
| oxine | 0.4% |
| in 0.05 N hydrochloric acid | |

Procedure

Measurement was carried out by the same procedure as in Example 3.

Results

The measurement results thus obtained are also shown in FIG. 2. In FIG. 2, -Δ- shows the results of measurement using the color producing solution containing 0.0125% of Methylxylenol Blue, - - the results of measurement using the color producing solution containing 0.01% of Methylxylenol Blue, and -∇- the results of measurement using the color producing solution containing 0.0075% of Methylxylenol Blue.

As is clear from FIG. 2, mere reductions of the amount of the chelating reagent at the time of measurement does not lower the color forming sensitivity but narrows the calibration range. On the other hand, according to the process of the present invention, the color forming sensitivity can be lowered without narrowing the calibration range.

EXAMPLE 4

Samples

Fifty human sera were used as samples.

Buffer Solution

The same buffer solution as in Example 3 was used.

Color Producing Solution

The same color producing solution as in Example 3 was used.

Procedure

Measurement was carried out by using a Hitachi automatic analyzer Model 7050 under the conditions shown in Table 2.

TABLE 2

| CHEMISTRY PARAMETERS | |
|---|---|
| ASSAY CODE | [1POINT]:[32]-[0] |
| SAMPLE VOLUME | [8] |
| R1 VOLUME | [400][50][NO] |
| R2 VOLUME | [200][50][NO] |
| WAVE LENGTH | [700][600] |
| CALIB. METHOD | [LINEAR][0] |
| STD. (1)CONC. -POS. | [0]-[1] |
| STD. (2)CONC. -POS | [10.0]-[2] |
| STD. (3-6)CONC. -POS | [0]-[0] |
| UNIT | [MG/DL] |
| SD LIMIT | [↓] |
| DUPLICATE LIMIT | [10000] |
| SENSITIVITY LIMIT | [0] |
| ABS. LIMIT (INC/DEC) | [↓][↓] |
| PROZONE LIMIT | [↓][↓] |
| EXPECTED VALUE | [ ]-[ ] |
| INSTRUMENT FACTOR | [1.00] |

COMPARATIVE EXAMPLE 4

Samples

The same samples as in Example 4 were used.

Buffer Solution

The same buffer solution as in Comparative Example 1 was used.

Color Producing Solution

The same color producing solution as in Comparative Example 1 was used.

Procedure

Measurement was carried out by using a Hitachi automatic analyzer Model 7050 under the conditions shown in Table 2, except that SAMPLE VOLUME was changed to 5, R1 VOLUME to 400, R2 VOLUME to 100, and WAVE LENGTH to [600][570].

Results

FIG. 3 shows a correlational diagram prepared on the basis of measured values obtained in Example 4 and Comparative Example 4. The correlation coefficient and the regression line formula obtained by statistical processing of the measured values were as follows:

Correlation coefficient: $\gamma = 0.988$

Regression line formula: $Y = 0.99 \times -0.01$ wherein

Y: the measured value obtained by Example 4

X: the measured value obtained by Comparative Example 4

As is clear from the above results, the measured values obtained by the process of the present invention were in good correlation with those obtained by a conventional method.

When investigated by use of the same reagent solution as in Example 4, the influence of the presence of bilirubin or ascorbic acid in a sample on measured values was not observed at all. In addition, the influence of hemolysis was investigated in the same manner as described above, but was hardly observed.

EXAMPLES 5

Measurement of Bismuth and Yttrium

Samples

Solutions containing predetermined concentrations of bismuth ($Bi^{3+}$) or yttrium ($Y^{3+}$) were used as samples.

Buffer Solution

There was used 5% triethanolamine buffer (pH 7.0).

Color Producing Solutions

Solutions containing predetermined concentrations of Methylxylenol Blue (MXB) and predetermined concentrations of sodium 2-[3-[N,N-bis(carboxymethyl-)aminomethyl]-4-hydroxy-2,5-dimethylbenzoyl]benzenesulfonate were used as color producing solutions.

Procedure

After 40 μl of each sample, 2.0 ml of the buffer solution and 1.0 ml of each color producing solution were thoroughly mixed and then allowed to stand at room temperature for 5 minutes, absorbance at a predetermined wavelength (bismuth: $OD_{480\ nm}$, yttrium: $OD_{570\ nm}$) was measured.

Results

Figure 4:
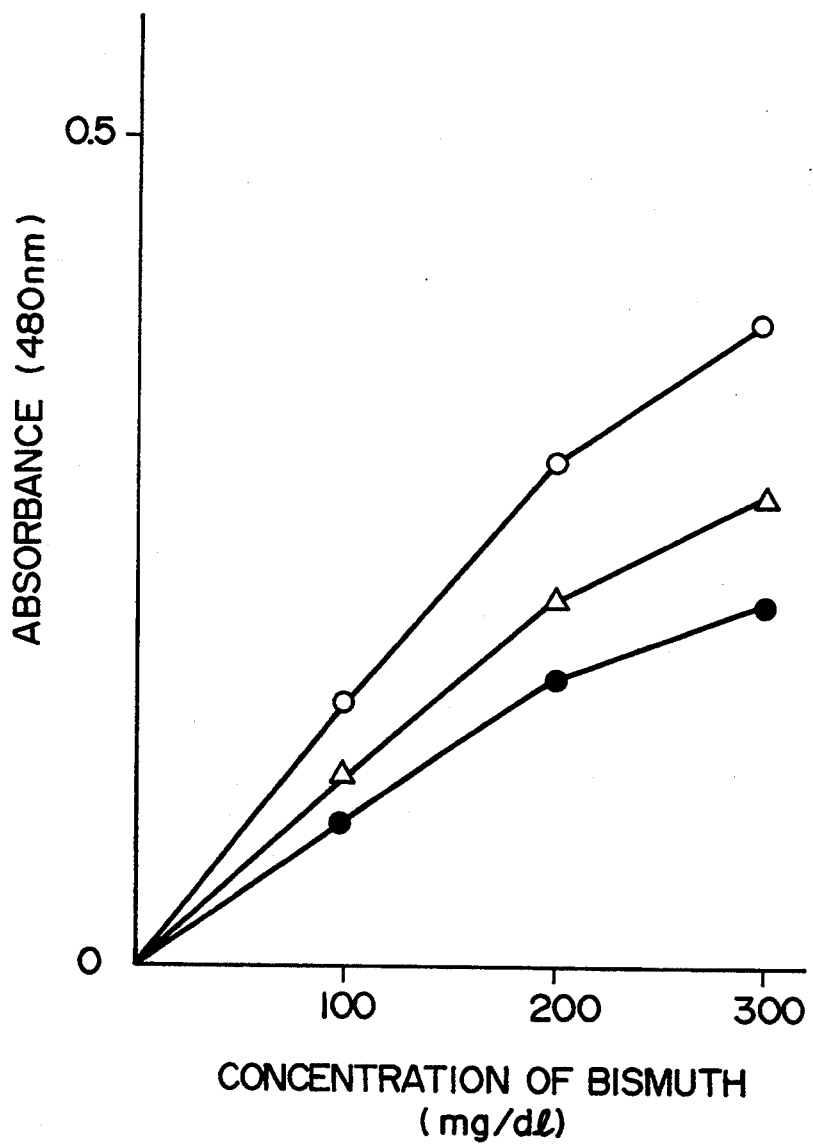
FIG. 4 and FIG. 5 show calibration curves obtained in Example 5.
Figure 5:
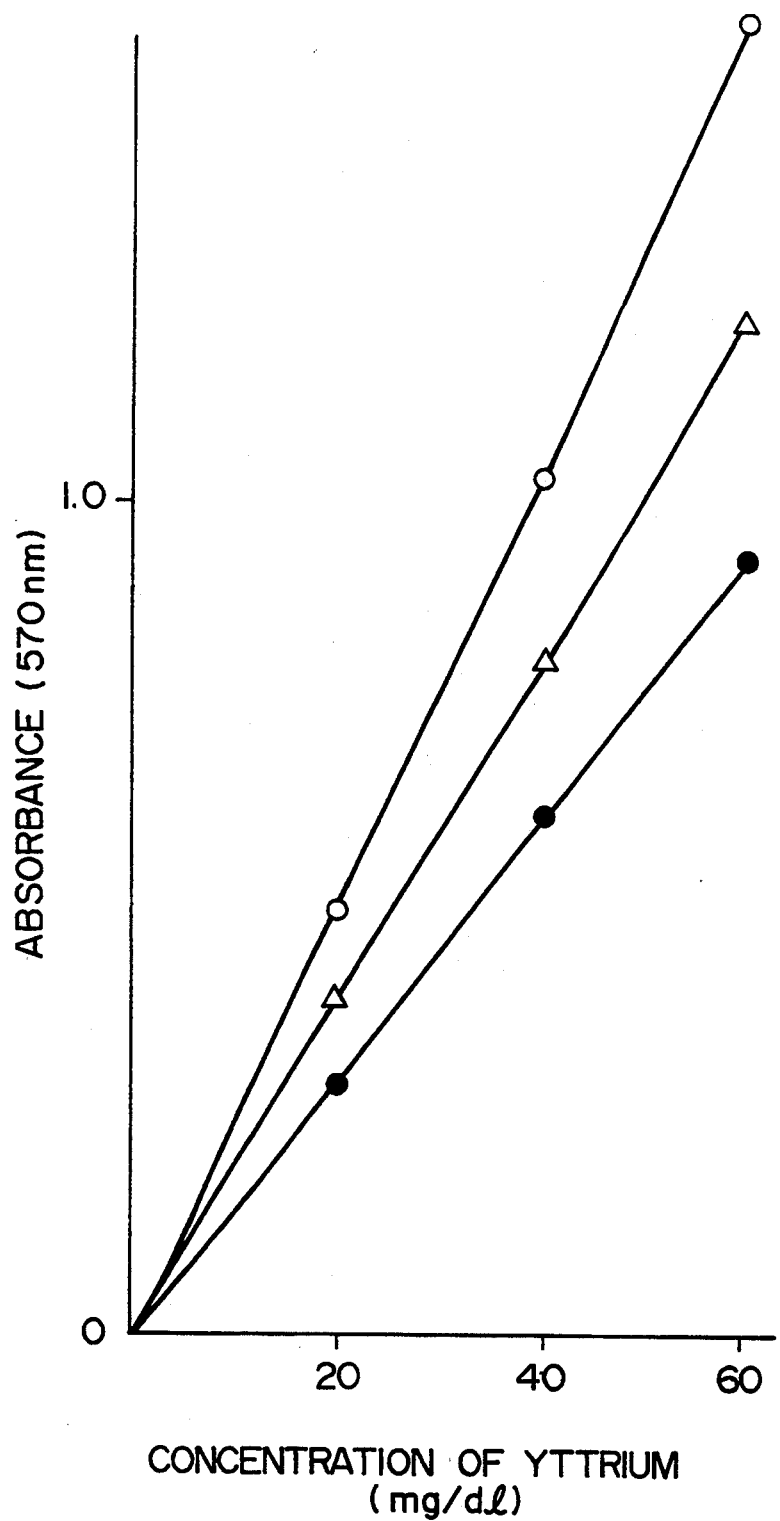

The measurement results thus obtained are shown in FIG. 4 and FIG. 5. FIG. 4 is a graph obtained by plotting absorbance on the axis of ordinate corresponding to individual bismuth concentrations (mg/dl) on the axis of abscissa. In FIG. 4, -○- shows the results of measurement using a color producing solution containing 0.02% of Methylxylenol Blue alone, -△- the results of measurement using a color producing solution containing 0.0133% of Methylxylenol Blue and 0.0067% of sodium 2-[3-[N,N-bis(carboxymethyl)aminomethyl]-4-hydroxy-2,5-dimethylbenzoyl]benzenesulfonate, and - - the results of measurement using a color producing solution containing 0.01% of Methylxylenol Blue and 0.01% of sodium 2-[3-[N,N-bis(carboxymethyl-)aminomethyl]-4-hydroxy-2,5-dimethylbenzoyl]benzenesulfonate. FIG. 5 is a graph obtained by plotting absorbance on the axis of ordinate corresponding to individual yttrium concentrations (mg/dl) on the axis of abscissa. In FIG. 5, -○- shows the results of measurement using the color producing solution containing 0.02% of Methylxylenol Blue alone, -△- the results of measurement using the color producing solution containing 0.0133% of Methylxylenol Blue and 0.0067% of sodium 2-[3-[N,N-bis(carboxymethyl)aminomethyl]-4-hydroxy-2,5dimethylbenzoyl]benzenesulfonate, and - - the results of measurement using the color producing solution containing 0.01% of Methylxylenol Blue and 0.01% of sodium 2-[3-[N,N-bis(carboxymethyl-)aminomethyl]-4-hydroxy-2,5-dimethylbenzoyl]benzenesulfonate.

As is clear from FIG. 4 and FIG. 5, in measuring bismuth or yttrium by use of Methylxylenol Blue as a chelating reagent to produce color, the measurement sensitivity can be adjusted by adding sodium 2-[3-[N,N-bis(carboxymethyl)aminomethyl]-4-hydroxy-2,5-dimethylbenzoyl]benzenesulfonate which is a phenol derivative of the present invention.

EXAMPLE 6

Measurement of Magnesium and Strontium

Samples

Solution containing predetermined concentrations of magnesium ($Mg^{2+}$) or strontium ($Sr^{2+}$) were used as samples.

Buffer Solution

There was used 5% monoethanolamine buffer (pH 11.0).

Color Producing Solutions

The same color producing solutions as in Example 5 were used.

Procedure

After 40 µl of each sample, 2.0 ml of the buffer solution and 1.0 ml of each color producing solution were thoroughly mixed and then allowed to stand at room temperature for 5 minutes, absorbance at a predetermined wavelength (magnesium: $OD_{600}$, strontium: $OD_{610\ nm}$) was measured.

Results

Figure 7:
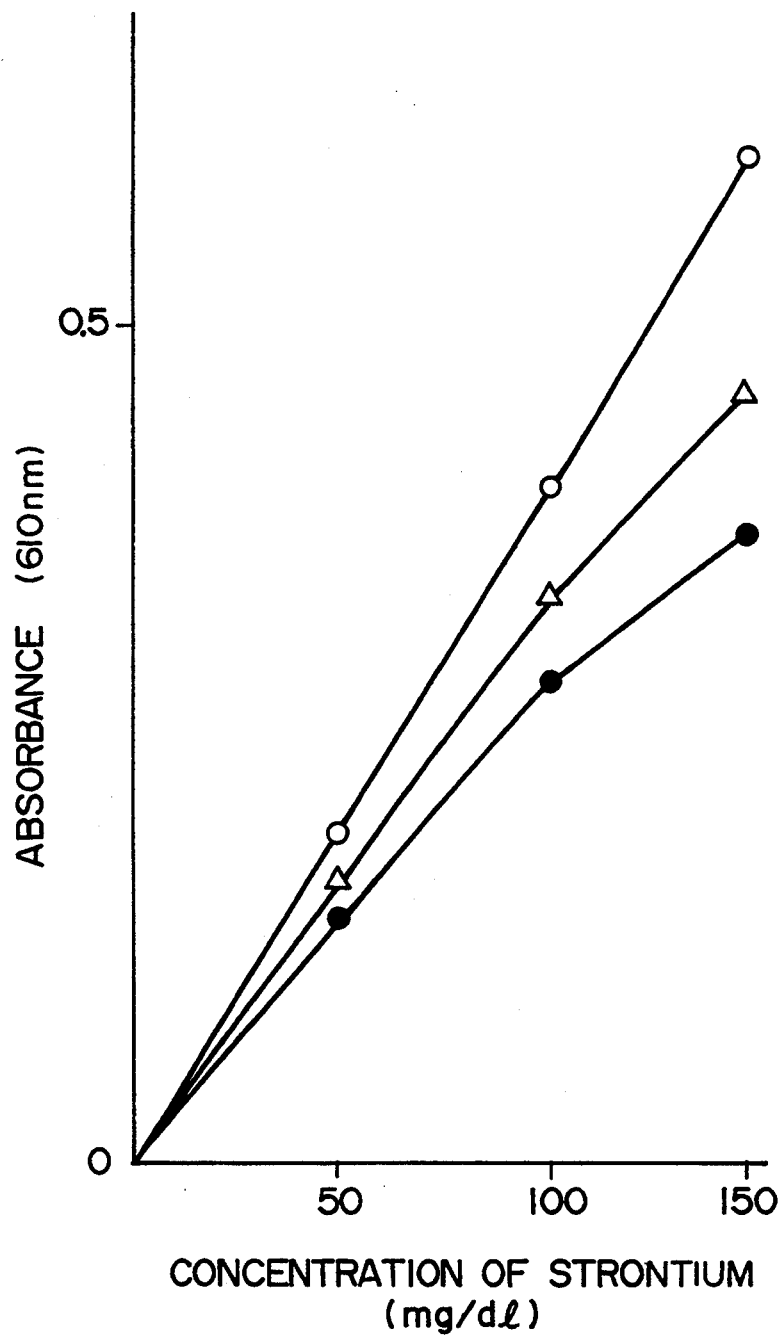

The measurement results thus obtained are shown in FIG. 6 and FIG. 7. FIG. 6 is a graph obtained by plotting absorbance on the axis of ordinate corresponding to individual magnesium concentrations (mg/dl) on the axis of abscissa. In FIG. 6, -◯- shows the results of measurement using the color producing solution containing 0.02% of Methylxylenol Blue alone, -△- the results of measurement using the color producing solution containing 0.0133% of Methylxylenol Blue and 0.0067% of sodium 2-[3-[N,N-bis(carboxymethyl)aminomethyl]-4-hydroxy-2,5-dimethylbenzoyl]benzenesulfonate, and -  - the results of measurement using the color producing solution containing 0.01% of Methylxylenol Blue and 0.01% of sodium 2-[3-[N,N-bis(-carboxymethyl)aminomethyl]-4-hydroxy-2,5-dimethylbenzoyl]benzenesulfonate. FIG. 7 is a graph obtained by plotting absorbance on the axis of ordinate corresponding to individual strontium concentrations (mg/dl) on the axis of abscissa. In FIG. 7, -◯- shows the results of measurement using the color producing solution containing 0.02% of Methylxylenol Blue alone, -△- the results of measurement using the color producing solution containing 0.0133% of Methylxylenol Blue and 0.0067% of sodium 2-[3-[N,N-bis(carboxymethyl)aminomethyl]-4-hydroxy-2,5-dimethylbenzoyl]benzenesulfonate, and -  - the results of measurement using the color producing solution containing 0.01% of Methylxylenol Blue and 0.01% of sodium 2-[3-[N,N-bis(-carboxymethyl)aminomethyl]-4-hydroxy-2,5-dimethylbenzoyl]benzenesulfonate.

As in clear from FIG. 6 and FIG. 7, in measuring magnesium or strontium by use of Methylxylenol Blue as a chelating reagent to produce color, the measurement sensitivity can be adjusted by adding sodium 2-[3-[N,N-bis(carboxymethyl)aminomethyl]-4-hydroxy-2,5-dimethylbenzoyl]benzenesulfonate which is a phenol derivative of the present invention.

As described above, the present invention provides a process for a colorimetric analysis of metal ions by use of a chelating reagent, which is characterized in that it makes it possible to lower the measurement sensitivity without narrowing the calibration range, and that it hardly produces measurement errors due to measuring temperature, as compared with conventional methods. Thus, the present invention contributes greatly to the art.

What is claimed is:

1. In a method for the colorimetric analysis of ions of a metal, said metal being selected from the group consisting of alkaline earth metals, heavy metals and rare earth metals, by reacting the metal ions with a chelating agent selected from the group consisting of phthalein complexone, methylxylenol blue, methylthymol blue and xylylazo violet and which forms a colored chelate with the metal ions, and colorimetrically detecting said colored chelate;

the improvement which comprises lowering the color forming sensitivity of the colored chelate by adding a phenol compound of the formula

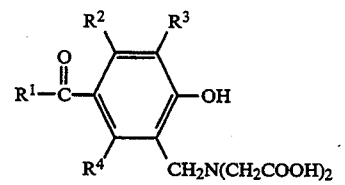

wherein $R^1$ is selected from the group consisting of a hydroxyl group; a halogen atom; an alkyl group optionally substituted by one or more substituents selected from the group consisting of a halogen atom, a hydroxyl group, a carboxyl group and a sulfonic acid group; an aryl group optionally substituted by one or more substituents selected from the group consisting of a hydroxyl group, a sulfonic acid group, an alkyl group and a halogen atom; and a heterocyclic group optionally substituted by one or more substituents selected from the group consisting of a hydroxyl group, a carboxyl group, sulfonic acid group, an alkyl group and a halogen atom; and $R^2$, $R^3$ and $R^4$ are independently selected from the group consisting of a hydrogen atom, a lower alkyl group, a lower alkoxy group and a halogen atom;

to a reagent solution for the colorimetric analysis of said metal ions containing said chelating agent, said phenol compound forming a colorless metal chelate with the metal ions thereby adjusting said color forming sensitivity.

2. A method according to claim 1, wherein the metal ions are present in a body fluid.

3. A method according to claim 1, wherein the metal ions are present in water.

4. A method according to claim 1, wherein the metal ions are selected from the group consisting of calcium ions and magnesium ions.

* * * * *